United States Patent
Yu et al.

(10) Patent No.: US 10,710,974 B2
(45) Date of Patent: Jul. 14, 2020

(54) METHOD FOR PREPARING EPSILON-CAPROLACTONE

(71) Applicant: SOUTH CHINA UNIVERSITY OF TECHNOLOGY, Guangdong (CN)

(72) Inventors: Hao Yu, Guangdong (CN); Mengmeng Hou, Guangdong (CN); Feng Peng, Guangdong (CN); Yonghai Cao, Guangdong (CN); Hongjuan Wang, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 16/332,796

(22) PCT Filed: Dec. 7, 2016

(86) PCT No.: PCT/CN2016/108767
§ 371 (c)(1),
(2) Date: Mar. 13, 2019

(87) PCT Pub. No.: WO2018/049733
PCT Pub. Date: Mar. 22, 2018

(65) Prior Publication Data
US 2019/0367470 A1 Dec. 5, 2019

(30) Foreign Application Priority Data
Sep. 13, 2016 (CN) .......................... 2016 1 0822731

(51) Int. Cl.
*C07D 313/04* (2006.01)
*B01J 21/18* (2006.01)

(52) U.S. Cl.
CPC .......... *C07D 313/04* (2013.01); *B01J 21/185* (2013.01)

(58) Field of Classification Search
CPC ............................. C07D 313/04; B01J 21/185
USPC ........................................................ 549/266
See application file for complete search history.

(56) References Cited

U.S. PATENT DOCUMENTS 4,013,691 A * 3/1977 Maki .................... B01J 31/1815
549/272

FOREIGN PATENT DOCUMENTS

| CN | 102391238 | | 3/2012 | | |
|---|---|---|---|---|---|
| CN | 102408404 | | 4/2012 | | |
| CN | 102603446 | | 7/2012 | | |
| CN | 103274883 | | 9/2013 | | |
| CN | 103980078 | * | 8/2014 | | |
| CN | 105440005 | | 3/2016 | | |
| CN | 105440006 | | 3/2016 | | |
| CN | 108558819 A | * | 9/2018 | ............. | C07C 57/04 |
| WO | WO-2015083185 A1 | * | 6/2015 | ........... | C07D 313/04 |

OTHER PUBLICATIONS

Kaneda; J. Org. Chem. 1994, 59, 11, 2915-2917. (Year: 1994).*
Unverified Machine Translation of Chinese Patent Application CN-103274883-A, Published on Jun. 8, 2013. (Year: 2013).*
Unverified Machine Translation of Chinese Patent Application CN-102603446-A, Published on Feb. 13, 2012. (Year: 2012).*
Yang; Catalysis Letters 2015, 145, 1955-1960. (Year: 2015).*
Ding Songdong et al., "Synthesis of ε-caprolactone", Chemical Reagents, Dec. 15, 2003, pp. 363-364.
Yuta Nabae et al., "Catalysis by Carbon Materials for the Aerobic Baeyer—Villiger Oxidation in the Presence of Aldehydes", 2013 American Chemical Society, Jan. 8, 2013, pp. 230-236.
Yue-Fang Li et al., "Graphite as a highly efficient and stable catalyst for the production of lactones", Carbon, Dec. 2012, pp. 269-275.
Li Yuefang, "The Catalytic Study on the Oxidation of Cyclohexanone into ε-Caprolactone and the Conversion of CH3Br Into p-Xylene or Light Olefins", Thesis of Master of Engineering, Hunan University, Sep. 2013, pp. 1-72.
Zhang Yadong et al., "Synthesis of ε-caprolactone with Fe—Sn Mixed Oxides as Catalysts", Journal of Zhengzhou University(Engineering Science), Jul. 2016, pp. 26-30.
"International Search Report (Form PCT/ISA/210)" dated Jun. 19, 2017, with English translation thereof, pp. 1-6.

* cited by examiner

*Primary Examiner* — Daniel R Carcanague
(74) *Attorney, Agent, or Firm* — JCIPRNET

(57) ABSTRACT

The present invention discloses a method for preparing ε-caprolactone. The method comprises the steps of: adding cyclohexanone, a co-oxidant and a certain amount of catalyst into a certain amount of organic solvent, using molecular oxygen as an oxidant, implementing a reaction with stirring for 0.1 to 24 hours under a pressure of 0.1 to 2 MPa and at a temperature of 60° C. to 100° C., wherein the co-oxidant is acrolein, and the catalyst is a carbon material. The present invention has the advantages of high-efficiency co-oxidant, easily available and recovered catalyst, environmental-friendly oxidant, simple operation and low cost.

5 Claims, 2 Drawing Sheets

METHOD FOR PREPARING EPSILON-CAPROLACTONE

TECHNICAL FIELD

The present invention relates to the field of preparation of an organic compound, and more particularly, to a method for preparing ε-caprolactone.

BACKGROUND

Baeyer-Villiger oxidation reaction is an important reaction to oxidize a cyclic ketone or a linear ketone into a more complicated and valuable linear ester or lactone. As an important polyester monomer, ε-caprolactone is mainly used to synthesize poly ε-caprolactone, and can be copolymerized or blended with various resins to improve the gloss, transparency and anti-adhesion of products. With the enhancement of people's awareness on environmental protection, it is also expected to replace the current common plastics to launch into the market of disposable packaging materials and plastic films in quantity, and has a broad prospect. In view of the factors such as raw materials, equipment and reaction conditions, a cyclohexanone oxidation method is the most effective method and is also the current method for industrial production of ε-caprolactone (Chemical Reagent, 2003, 25(6):363-364).

According to different oxidants used in the reaction, the cyclohexanone oxidation method can be divided into four methods: a peroxyacid oxidation method, a $H_2O_2$ oxidation method, a biological oxidation method and a molecular oxygen oxidation method. As an oxidant, molecular oxygen is an ideal oxidant for cyclohexanone oxidation since it overcomes the disadvantages of other three oxidation methods such as high risk, low yield and high cost, and has the advantages of safety, low cost, less by-products and less environmental pollution. However, due to the weak oxidizing ability of the molecular oxygen, direct oxidation of cyclohexanone with the molecular oxygen cannot achieve satisfactory results, and aldehyde co-oxidants and appropriate catalyst are usually added to oxidize cyclohexanone in the reaction process. Patent CN102408404A reports a method for preparing ε-caprolactone by oxidizing cyclohexanone through molecular oxygen. Although a catalyst is avoided in the reaction process, there are also potential safety hazards since azobisisobutyronitrile is used as an initiator. Moreover, using benzaldehyde as a co-oxidant causes difficulties for subsequent separation and purification, and increases the industrial cost. Patent CN102391238B uses a metalloporphyrin compound to catalyze cyclohexanone and the molecular oxygen to prepare ε-caprolactone by oxidation, which has high selectivity and a small amount of adjuvants, but a homogeneous catalyst is difficult to separate and expensive. Patents CN105440005A and CN 105440006A respectively propose methods for preparing ε-caprolactone by using magnesia-alumina hydrotalcite and $MgO/Fe_2O_3$ catalyst to catalyze and oxidize cyclohexanone, wherein molecular oxygen is used as an oxidant, and a solid catalyst is easy to recover. A non-metal carbon material has the characteristics of good stability and high catalytic activity. It is found by Nabae (ACS Catalysis, 2013, 3:230-236) et al. that Ketjen carbon black has good catalytic activity for the reaction of synthesizing the ε-caprolactone by oxidizing cyclohexanone, wherein a conversion of the cyclohexanone reaches 61%, and a yield of the ε-caprolactone reaches 61%. It is found by Li Yuefang (Carbon, 2013, 55:269-275) et al. that, at a room temperature, a conversion of ε-caprolactone, synthesized by oxidizing cyclohexanone catalyzed by graphite, is as high as 92.5%, and the selectivity of ε-caprolactone is 100%. Patent CN103274883A also discloses a method for catalyzing and oxidizing cyclohexanone to synthesize ε-caprolactone by using a carbon nanotube as a catalyst.

Aldehydes are mainly used as co-oxidants in the cyclohexanone molecular oxygen oxidation method, and the commonly used aldehyde co-oxidants comprise acetaldehyde, propionaldehyde, isobutyraldehyde, isovaleraldehyde, benzaldehyde, p-tolualdehyde and so on. Usually, benzaldehyde or p-tolualdehyde is the preferred co-oxidant (CN105440005A; CN105440006A; CN103274883A; CN102408404A; CN102391238B). However, a lower benzaldehyde efficiency (yield of ε-caprolactone/conversion of benzaldehyde) limits the economic feasibility of the cyclohexanone oxidation using molecular oxygen as oxidant. For example, the highest efficiency of the benzaldehyde reported by Nabae (ACS Catalysis, 2013, 3:230-236) et al. is 0.77. Moreover, the benzaldehyde is converted into benzoic acid in the reaction process, and the value thereof is reduced. Therefore, on the basis of satisfying the reaction stoichiometry between cyclohexanone and co-oxidant, to develop a co-oxidant with low molecular weight and high efficiency is of great significance to improve the economy of the process. Acrolein and acrylic acid are both value-added chemical intermediates in the chemical industry. Up to now, there have been no reports on the use of acrolein as co-oxidant for Baeyer-Villiger oxidation of cyclohexanone.

SUMMARY

The present invention is intended to solve the problems of low efficiency and high cost of benzaldehyde as co-oxidant in the existing Baeyer-Villiger oxidation of cyclohexanone using $O_2$/aldehyde system, which combines a novel co-oxidant, acrolein, together with a nitrogen-doped carbon nanotube as a metal-free catalyst, and creates a method for synthesizing ε-caprolactone with the advantages of simple operation, easy recycling of catalyst, and low cost.

The purpose of the present invention is achieved through the following technical solutions.

A preparation method of ε-caprolactone comprises the following steps:

adding cyclohexanone, a co-oxidant and a catalyst into an organic solvent, using molecular oxygen as an oxidant, performing a reaction with stirring for 0.1 to 24 hours under a pressure of 0.1 to 2 MPa and at a temperature of 60° C. to 100° C., and obtaining the ε-caprolactone; wherein the co-oxidant is an aldehyde, and the catalyst is a carbon material.

Preferably, the organic solvent is one or more than one of 1,2-dichloroethane, carbon tetrachloride, acetonitrile, dichloromethane and toluene.

Preferably, the co-oxidant is acrolein.

Preferably, the catalyst is one or more than one of a nitrogen-doped carbon nanotube (NCNT), a carbon nanotube (CNT), a carboxylated carbon nanotube ($HNO_3$+CNT) and activated carbon.

Preferably, a mass ratio of the organic solvent to cyclohexanone is (6 to 799):1.

Preferably, a molar ratio of the co-oxidant to cyclohexanone is (0.25 to 100):1.

Preferably, a mass ratio of the catalyst to cyclohexanone is (0.01 to 2):1.

Preferably, the temperature of the reaction is 60° C. to 80° C., the pressure of the reaction is 0.1 to 1 MPa, and the reaction lasts for 0.1 to 4 hours.

Compared with the prior art, the present invention has the following advantages.

(1) Acrolein is used as the co-oxidant according to the present invention, and acrylic acid with higher industrial value is obtained after reaction, which improves the economic feasibility of the process. The efficiency of acrolein (the ratio of the yield of the ε-caprolactone to the conversion of acrolein) can reach 100% when the molar ratio of aldehydes to ketones is greater than 4, which can significantly reduce the consumption of the co-oxidant. Meanwhile, in comparison to the common co-oxidant benzaldehyde, a difference of boiling points between the acrylic acid (the oxidation product of acrolein) and the ε-caprolactone is larger, which is more conducive to the separation and purification of the product.

(2) The nitrogen-doped carbon nanotube is used as the catalyst in the present invention, which has the advantages of high activity, easily available and recovered catalyst, and environmental protection.

DETAILED DESCRIPTION

The present invention is further described hereinafter with reference to the embodiments and the accompanied drawings, but the scope of protection of the present invention is not limited to the description of the embodiments.

Figure 1:
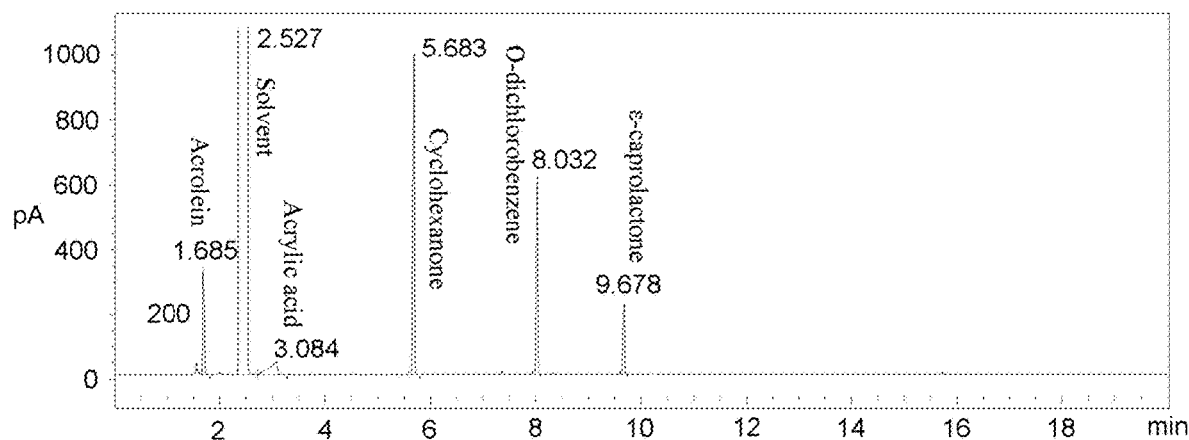
FIG. 1 is a gas chromatogram of a reaction liquid after reaction in a third embodiment.
Figure 2:
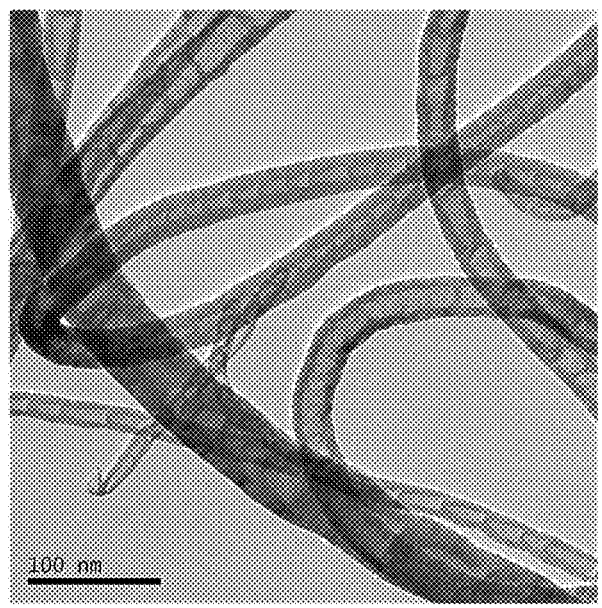
FIG. 2 is a transmission electron micrograph (TEM) of a nitrogen-doped carbon nanotube used in the present invention.
Figure 3:
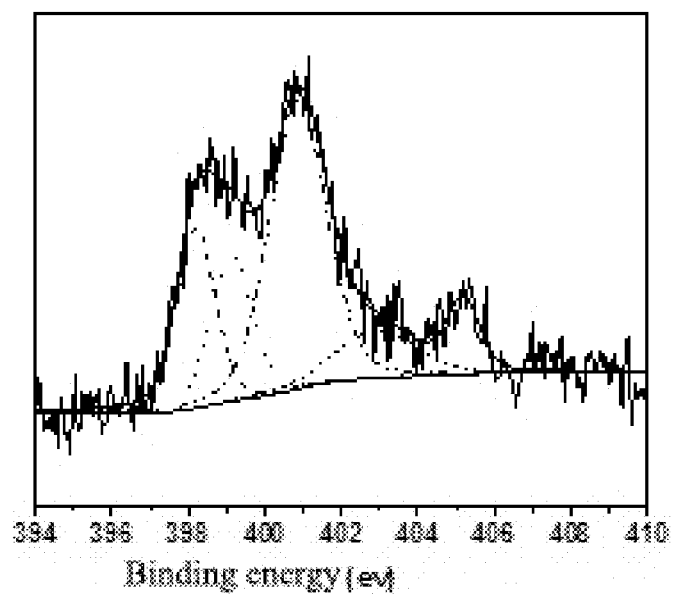
FIG. 3 is an XPS spectrum of the nitrogen-doped carbon nanotube used in the present invention.

A transmission electron micrograph (TEM) and an $N_{1s}$ XPS spectrum of a nitrogen-doped carbon nanotube used in the present invention are as shown in FIG. 2 and FIG. 3. The result shows that a content of N is 4.34 at %.

In the following embodiments, conversion (%) of cyclohexanone and acrolein, and selectivities (%) of ε-caprolactone and acrylic acid are analyzed and measured by a gas chromatography (GC). An internal standard method is used in GC detection and calculation, o-dichlorobenzene is used as an internal standard substrate, and standard curves corresponding to four substrates are plotted respectively, which are then combined with the GC detection and calculation of a reaction solution to obtain the results.

Embodiments 1 to 5

25 ml of 1,2-dichloroethane, 2.6 g of o-dichlorobenzene (internal standard substance), 4.75 g of cyclohexanone, 2.69 g of acrolein and 100 mg of nitrogen-doped carbon nanotube (a content of N was 4.34 at %) were sequentially added into a high-pressure reactor, stirred and heated to a temperature shown in Table 1, and charged with oxygen; then, timing was started, and the pressure was maintained at 1 MPa during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). After the reaction in the Embodiment 3, a gas chromatogram of the reaction solution was shown in FIG. 3. GC measurement results were shown in Table 1 (effects of the reaction temperature on the Baeyer-Villiger oxidation of cyclohexanone).

TABLE 1

| | Embodiment | | | | |
|---|---|---|---|---|---|
| | 1 | 2 | 3 | 4 | 5 |
| Reaction temperature (° C.) | 60 | 70 | 80 | 90 | 100 |
| Conversion of cyclohexanone (%) | 0.93 | 16 | 22 | 32 | 43 |
| Selectivity of ε-caprolactone (%) | 100 | 78 | 74 | 66 | 65 |
| Conversion of acrolein (%) | 7 | 16 | 37 | 61 | 86 |
| Selectivity of acrylic acid (%) | 100 | 100 | 100 | 82 | 80 |
| Efficiency of acrolein | 0.13 | 0.78 | 0.44 | 0.35 | 0.32 |

It can be seen from Table 1 that temperature increase is favorable for oxidation of cyclohexanone, but when the temperature reaches 90° C., the selectivities of ε-caprolactone and acrylic acid, especially the selectivity of acrylic acid, are greatly decreased while the conversion are increased. Therefore, the optimal temperature is 80° C. on the premise of ensuring the high yield of ε-caprolactone and 100% selectivity of acrylic acid.

Embodiments 6 to 12

25 ml of 1,2-dichloroethane, 2.6 g of o-dichlorobenzene (internal standard substance), 4.75 g of cyclohexanone, 2.69 g of acrolein and 100 mg of nitrogen-doped carbon nanotube (a content of N was 4.34 at %) were sequentially added into a high-pressure reactor, stirred and heated to a temperature of 80° C., and charged with oxygen; then, timing was started, and the pressure was maintained at 1 MPa during the reaction. After reaction for a time shown in Table 2, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 2 (effects of the reaction time on the Baeyer-Villiger oxidation of cyclohexanone).

TABLE 2

| Embodiment | 6 | 7 | 8 | 3 | 9 | 10 | 11 | 12 |
|---|---|---|---|---|---|---|---|---|
| Reaction time (h) | 0.1 | 2 | 3 | 4 | 6 | 8 | 12 | 24 |
| Conversion of cyclohexanone (%) | 2 | 13 | 19 | 22 | 27 | 33 | 40 | 45 |
| Selectivity of ε-caprolactone (%) | 91 | 81 | 78 | 74 | 71 | 62 | 63 | 60 |
| Conversion of acrolein (%) | 2 | 13 | 29 | 37 | 49 | 64 | 79 | 90 |
| Selectivity of acrylic acid (%) | 100 | 100 | 100 | 100 | 98 | 81 | 82 | 80 |
| Efficiency of acrolein | 0.91 | 0.81 | 0.51 | 0.44 | 0.39 | 0.32 | 0.31 | 0.30 |

Through analyzing the data in Table 2, it can be known that the conversion of cyclohexanone is increased with the extension of time, the efficiency of acrolein is decreased with the increase of the conversion of acrolein, and the selectivity of acrylic acid is obviously decreased after 4 hours. The optimal duration within the time range studied in Table 2 is 4 hours on the premise of ensuring the high yield of ε-caprolactone and 100% selectivity of acrylic acid.

Embodiments 13 to 16

25 ml of 1,2-dichloroethane, 2.6 g of o-dichlorobenzene (internal standard substance), 4.75 g of cyclohexanone, 2.69 g of acrolein and 100 mg of nitrogen-doped carbon nanotube (a content of N was 4.34 at %) were sequentially added into a high-pressure reactor, stirred and heated to a temperature of 80° C., and charged with oxygen; then, timing was started, and the mixture was maintained at a pressure shown in Table 3 during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 3 (effects of the reaction pressure on the Baeyer-Villiger oxidation of cyclohexanone).

TABLE 3

|  | Embodiment | | | | |
| --- | --- | --- | --- | --- | --- |
|  | 13 | 14 | 3 | 15 | 16 |
| Reaction pressure (MPa) | 0.1 | 0.5 | 1 | 1.5 | 2 |
| Conversion of cyclohexanone (%) | 13 | 19 | 22 | 24 | 27 |
| Selectivity of ε-caprolactone (%) | 88 | 81 | 74 | 70 | 64 |
| Conversion of acrolein (%) | 15 | 30 | 37 | 43 | 48 |
| Selectivity of acrylic acid (%) | 100 | 100 | 100 | 95 | 89 |
| Efficiency of acrolein | 0.76 | 0.51 | 0.44 | 0.39 | 0.36 |

Through analyzing the data in Table 3, it can be known that the conversion of cyclohexanone is not increased obviously with the increase of pressure, while the efficiency of acrolein is decreased with the increase of pressure, and the selectivity of acrylic acid is obviously decreased after the pressure is greater than 1 MPa. The optimal pressure within the pressure range in Table 3 is 1 MPa on the premise of ensuring the high yield of ε-caprolactone and 100% selectivity of acrylic acid.

Embodiments 17 to 20

25 ml of 1,2-dichloroethane, 2.6 g of o-dichlorobenzene (internal standard substance), 4.75 g of cyclohexanone, 2.69 g of acrolein and 100 mg of catalyst as shown in FIG. 4 were sequentially added into a high-pressure reactor, stirred and heated to a temperature of 70° C., and charged with oxygen; then, timing was started, and the pressure was maintained at 1 MPa during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 4 (effects of different carbon materials on the Baeyer-Villiger oxidation of cyclohexanone).

TABLE 4

|  | Embodiment | | | |
| --- | --- | --- | --- | --- |
|  | 17 | 18 | 19 | 20 |
| Carbon material | NCNT | CNT | HNO$_3$ + CNT | Activated carbon |
| Conversion of cyclohexanone (%) | 16 | 12 | 4 | 5 |
| Selectivity of ε-caprolactone (%) | 78 | 67 | 96 | 90 |
| Conversion of acrolein (%) | 16 | 65 | 11 | 11 |
| Selectivity of acrylic acid (%) | 100 | 48 | 76 | 100 |
| Efficiency of acrolein | 0.77 | 0.12 | 0.38 | 0.43 |

Through analyzing the data in Table 4, it can be known that the nitrogen-doped carbon nanotube (a content of N is 4.34 at %) has the optimal catalytic activity.

Embodiments 21 to 24

25 ml of 1,2-dichloroethane, 2.6 g of o-dichlorobenzene (internal standard substance), 4.75 g of cyclohexanone, 2.69 g of acrolein and nitrogen-doped carbon nanotube (a content of N was 4.34 at %) with an amount as shown in FIG. 5 were sequentially added into a high-pressure reactor, stirred and heated to a temperature of 80° C., and charged with oxygen; then, timing was started, and the pressure was maintained at 1 MPa during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 5 (effects of the nitrogen-doped carbon nanotube of different amounts on the Baeyer-Villiger oxidation of cyclohexanone).

TABLE 5

|  | Embodiment | | | | |
| --- | --- | --- | --- | --- | --- |
|  | 21 | 22 | 23 | 3 | 24 |
| Amount of nitrogen-doped carbon nanotube (mg) | 0 | 60 | 80 | 100 | 120 |
| Conversion of cyclohexanone (%) | <1 | 17 | 19 | 22 | 21 |
| Selectivity of ε-caprolactone (%) | — | 81 | 76 | 74 | 73 |
| Conversion of acrolein (%) | <1 | 32 | 34 | 37 | 41 |
| Selectivity of acrylic acid (%) | — | 100 | 100 | 100 | 99 |
| Efficiency of acrolein | — | 0.43 | 0.42 | 0.44 | 0.37 |

It can be known from Table 5 that when the amount of the catalyst is 100 mg, the yields of ε-caprolactone and acrylic acid are both the highest, and the efficiency of acrolein is also the largest while ensuring 100% selectivity of acrylic acid.

Embodiments 25 to 28

25 ml of a solvent as shown in FIG. 6, 2.6 g of o-dichlorobenzene (internal standard substance), 4.75 g of cyclohexanone, 2.69 g of acrolein and 100 mg of nitrogen-doped carbon nanotube (a content of N was 4.34 at %) were sequentially added into a high-pressure reactor, stirred and heated to a temperature of 80° C., and charged with oxygen; then, timing was started, and the pressure was maintained at 1 MPa during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 6 (effects of different solvents on the Baeyer-Villiger oxidation of cyclohexanone).

TABLE 6

|  | Embodiment | | | | |
| --- | --- | --- | --- | --- | --- |
|  | 3 | 25 | 26 | 27 | 28 |
| Different solvents | 1,2-dichloroethane | Carbon tetrachloride | Acetonitrile | Dichloromethane | Toluene |
| Conversion of cyclohexanone (%) | 22 | 22 | 14 | 18 | 15 |
| Selectivity of ε-caprolactone (%) | 74 | 54 | 73 | 75 | 54 |
| Conversion of acrolein (%) | 37 | 50 | 34 | 35 | 25 |
| Selectivity of acrylic acid (%) | 100 | 79 | 100 | 96 | 100 |
| Efficiency of acrolein | 0.44 | 0.24 | 0.30 | 0.39 | 0.32 |

It can be known from Table 6 that when 1,2-dichloroethane is used as the solvent, the yields of ε-caprolactone and acrylic acid and the efficiency of acrolein are all the highest.

Embodiments 29 to 36

A certain volume of 1,2-dichloroethane (ensuring that a mass ratio of the solvent to cyclohexanone was 6 to 799), 2.6 g of o-dichlorobenzene (internal standard substance), acrolein and cyclohexanone of various molar ratios as shown in Table 7 (wherein the amounts of cyclohexanone in Embodiments 29 to 31 were all 48 mmol, and the amounts of acrolein in Embodiments 32 to 36 were all 48 mmol) and 100 mg of nitrogen-doped carbon nanotube (a content of N was 4.34 at %) were sequentially added into a high-pressure reactor, stirred and heated to a temperature of 80° C., and charged with oxygen; then, timing was started, and the pressure was maintained at 1 MPa during the reaction. After reaction for 4 hours, timing was stopped, the reactor was cooled to a room temperature, and a liquid-solid phase mixture was filtered to obtain a solid catalyst and a liquid-phase mixture containing unreacted reactants and products. The liquid-phase mixture was measured by gas chromatography (GC). GC detection results were shown in Table 7 (effects of different molar ratios of aldehydes to ketones on the Baeyer-Villiger oxidation of cyclohexanone).

Through analyzing the data in Table 7, it can be known that the conversion of cyclohexanone is increased with the increase of the ratio of aldehydes to ketones, and when the ratio of aldehydes to ketones is 100, cyclohexanone can even be completely converted. After the ratio of aldehydes to ketones is greater than 4, the efficiency of acrolein is maintained at 100%, and the optimal molar ratio of aldehydes to ketones is 4.00 on the premise of ensuring the high yield of the ε-caprolactone and 100% selectivity of acrylic acid.

What is claimed is:

1. A preparation method of ε-caprolactone, comprising the following steps:
    adding cyclohexanone, a co-oxidant and a catalyst into an organic solvent, using molecular oxygen as an oxidant, performing a reaction with stirring for 0.1 to 24 hours under a pressure of 0.5 to 1 MPa and at a temperature of 60° C. to 100° C., and obtaining the ε-caprolactone and acrylic acid; wherein the co-oxidant is acrolein, and the catalyst is a nitrogen-doped carbon nanotube, wherein a molar ratio of the co-oxidant to cyclohexanone is (4 to 100):1.

2. The preparation method according to claim 1, wherein the organic solvent is one or more than one of 1,2-dichloroethane, carbon tetrachloride, acetonitrile, dichloromethane and toluene.

3. The preparation method according to claim 1, wherein a mass ratio of the organic solvent to the cyclohexanone is (6 to 799):1.

TABLE 7

| Embodiment | Ratio of aldehydes to ketones | Conversion of cyclohexanone (%) | Selectivity of ε-caprolactone (%) | Conversion of acrolein (%) | Selectivity of acrylic acid (%) | Efficiency of acrolein |
| --- | --- | --- | --- | --- | --- | --- |
| 29 | 0.25 | 5.78 | 59 | 27 | 100 | 0.13 |
| 30 | 0.5 | 11 | 69 | 27 | 100 | 0.28 |
| 3 | 1.00 | 22 | 74 | 37 | 100 | 0.44 |
| 31 | 1.25 | 30 | 73 | 49 | 96 | 0.45 |
| 32 | 2.00 | 30 | 82 | 33 | 100 | 0.75 |
| 33 | 4.00 | 46 | 82 | 38 | 100 | 1.00 |
| 34 | 8.00 | 66 | 83 | 54 | 78 | 1.00 |
| 35 | 16.00 | 74 | 77 | 57 | 71 | 1.00 |
| 36 | 100.00 | 100 | 62 | 62 | 68 | 1.00 |

4. The preparation method according to claim 1, wherein a mass ratio of the catalyst to cyclohexanone is (0.01 to 2):1.

5. The preparation method according to claim 1, wherein the temperature of the reaction is 60° C. to 80° C. and the reaction lasts for 0.1 to 4 hours.

* * * * *